(12) United States Patent
Markstroem (10) Patent No.: US 8,100,132 B2
(45) Date of Patent: Jan. 24, 2012

(54) FIXATION DEVICE

(75) Inventor: Marten Markstroem, Stockholm (SE)

(73) Assignee: Elekta AB (Publ), Stockholm (SE)

( * ) Notice: Subject to any disclaimer, the term of this patent is extended or adjusted under 35 U.S.C. 154(b) by 281 days.

(21) Appl. No.: 12/427,471

(22) Filed: Apr. 21, 2009

(65) Prior Publication Data

US 2009/0260636 A1    Oct. 22, 2009

(30) Foreign Application Priority Data

Apr. 22, 2008    (EP) .................................... 08154930

(51) Int. Cl.
 *A61G 12/00*  (2006.01)
 *A61F 5/37*  (2006.01)
 *A61B 3/16*  (2006.01)
 *A61B 6/08*  (2006.01)
 *A61B 19/00*  (2006.01)

(52) U.S. Cl. ........ 128/869; 128/845; 128/846; 600/415; 600/421; 378/205

(58) Field of Classification Search .................. 128/869, 128/846, 845; 600/415, 421; 433/41, 43, 433/57, 62, 68, 109, 157, 24; 403/83, 53, 403/55, 60, 63, 119; 362/285, 804, 451; 16/221, 226, 235; 378/205, 208–209, 195; 5/652, 637; 606/130

See application file for complete search history.

(56) References Cited

U.S. PATENT DOCUMENTS 4,782,503 A    11/1988 Molitor et al.

(Continued)

FOREIGN PATENT DOCUMENTS

EP    0 365 840 A1    9/1989

OTHER PUBLICATIONS

European Office Action dated Aug. 5, 2011. pp. 1-5.

*Primary Examiner* — Patricia Bianco
*Assistant Examiner* — George N Phillips
(74) *Attorney, Agent, or Firm* — Birch, Stewart, Kolasch & Birch, LLP (57) ABSTRACT

This invention relates to a fixation device for immobilizing a head of a patient relative a treatment unit or medical device during treatment of the head. The fixation device is provided with an interface unit adapted to be fixated in relation to an adaptor unit for connection to the treatment unit, or to a frame for connection to the medical device. Furthermore, the fixation device is further provided with a sliding plate being slidable in relation to said interface unit in an xz-plane of a coordinate system. The system is a Cartesian coordinate system defined by three orthogonal axis having an x-axis extending in the medial-lateral direction of the patient, an y-axis extending in the anterior-posterior direction, and a z-axis extending in the cranial-caudal direction. The fixation device is further provided with a plate locking means for locking said sliding plate in relation to said interface unit, a bite-block for being inserted into a mouth of the patient, a linking means for linking said bite-block with said sliding plate, at least one pivot point arranged such that the bite-block is movable at least in a plane orthogonal to the xz-plane; and a link locking means for locking said at least one pivot point in a desired position in relation to said linking means so as to fixate the bite-block to the interface unit.

20 Claims, 4 Drawing Sheets

U.S. PATENT DOCUMENTS

| | | | |
|---|---|---|---|
| 5,464,411 A * | 11/1995 | Schulte et al. | 606/130 |
| 5,836,878 A * | 11/1998 | Mock et al. | 600/415 |
| 6,143,003 A * | 11/2000 | Cosman | 606/130 |
| 6,243,439 B1 | 6/2001 | Arai et al. | |
| 6,424,694 B1 | 7/2002 | Molteni et al. | |
| 2011/0036356 A1 * | 2/2011 | Arn et al. | 128/845 |

* cited by examiner

FIXATION DEVICE

FIELD OF THE INVENTION

The present invention relates to the field of radiation therapy. In particular, the invention relates to a fixation device for immobilizing a head of a patient relative a treatment unit during treatment of the head.

BACKGROUND OF THE INVENTION

The development of surgical techniques have made great progress over the years. For instance, for patients requiring brain surgery, non-invasive surgery is now available which is afflicted with very little trauma to the patient.

Stereotactic radiation surgery is such a minimally invasive treatment modality that allows delivery of a large single dose of radiation to a specific intracranial target while sparing surrounding tissue. Unlike conventional fractionated radiation therapy, stereotactic radiation surgery does not rely on, or exploit, the higher radiation sensitivity of neoplastic lesions relative to normal brain (therapeutic ratio). Its selective destruction depends primarily on sharply focused high-dose radiation and a steep dose gradient away from the defined target. The biological effect is irreparable cellular damage and delayed vascular occlusion within the high-dose target volume. Because a therapeutic ratio is not required, traditionally radiation resistant lesions can be treated. Because destructive doses are used, however, any normal structure included in the target volume is subject to damage.

One such non-invasive radiation therapy technique is so called LINAC (Linear Accelerator) radio therapy or radiation therapy. In a LINAC radiation therapy system, a collimated x-ray beam of a very high energy level is focused on a stereotactically identified intracranial target. In such an accelerator, electrons are accelerated to near light speed and are collided with a heavy metal, e.g. tungsten. The collision mainly produces heat but a small percentage of the energy is converted into highly energetic photons, which, because they are electrically produced, are called "x-rays". The gantry of the LINAC rotates around the patient, producing an arc of radiation focused on the target. The couch in which the patient rests is then rotated in the horizontal plane, and another arc is performed. In this manner, multiple non-coplanar arcs of radiation intersect at the target volume and produce a high target dose, resulting in a minimal radiation affecting the surrounding brain.

Another system for non-invasive surgery is sold under the name of Leksell Gamma Knife®, which provides such surgery by means of gamma radiation. The radiation is emitted from a large number of fixed radioactive sources and are focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all radiation sources intersect or converge, causing the radiation to reach tissue-destructive levels. The point of convergence is hereinafter referred to as the "focus point". Such a gamma radiation device is, for example, referred to and described in U.S. Pat. No. 4,780,898.

In the system, the head of a patient is immobilized in a stereotactic instrument which defines the location of the treatment volume in the head. Further, the patient is secured in a patient positioning unit which moves the entire patient so as to position the treatment volume in coincidence with the focus point of the radiation unit of the radiation therapy system.

Consequently, in radiation therapy systems, such as a LINAC system or a Leksell Gamma Knife® system, it is of a high importance that the positioning unit which moves the patient so as to position the treatment volume in coincidence with the focus point of the radiation unit of the system is accurate and reliable. That is, the positioning unit must be capable of position the treatment volume in coincidence with the focus point at a very high precision. This high precision must also be maintained over time.

Hence, in order to obtain as favorable clinical effect as possible during the therapy is it of an utmost importance that the radiation reaches and hits the target, i.e. the treatment volume, with a high precision and thereby spares the healthy tissue being adjacent to and/or surrounding the treatment volume. To achieve this, the patient must be immobilized during a therapy session and, moreover, the position of the head of the patient must be the same in a therapy session as in a reference position, i.e. the position during the session when the pictures to create the therapy plan were captured by means of, for example, Computerized Tomography Imaging (CT-imaging). In fractionated radiation therapy where the patient is docked in and out of the radiation therapy system at each therapy session, it must thus be secured that the patient is positioned in exact the same way as in the session when the pictures were captured to create the therapy plan.

One prior art method for enabling measurements of the head of a patient and for immobilizing or fixating the head of the patient during neurological diagnosis, therapy or surgery, in particular during radiation therapy relatively an interface unit, frame or adaptor adapted to be fixated to a radiation therapy unit is a stereotactic frame provided with pin support members in form of posts having fixation pins for invasive fixation to the skull of a patient. In use during therapy or diagnostics, the stereotactic frame is arranged around the head of a patient, and the fixation pins of the posts connected to the frame are screwed into or to abutment against the bone of the skull, thus ensuring a rigid fixation of the reference system. The frame is then rigidly held in position in relation to a patient table. This kind of frame is obviously not suitable for so called fractionated therapy.

Thus, there is a need for a head fixation arrangement that enables an accurate repeatable fixation of a head of a patient relative a radiation therapy unit during neurological diagnosis, therapy or surgery, to secure that the patient, or more specifically the head of the patient, is positioned in exact alignment to a reference position or at a known position in relation to the reference position, and that this done every single therapy occasion of the fractionated therapy.

SUMMARY OF THE INVENTION

An object of the present invention is to provide means for an accurate repeatable fixation of a head of a patient relative a treatment unit of a head treatment system during a treatment of the head or a portion thereof, to secure that the head of the patient is positioned and repositioned in exact alignment to a reference position or at a known position in relation to the reference position every single therapy occasion of a repeatable treatment.

This and other objects are achieved by providing a fixation device having the features defined in the independent claim. Example embodiments are defined in the dependent claims.

According to a first aspect of the present invention, there is provided a fixation device for immobilizing a head of a patient relative a treatment unit or medical device during treatment of the head. Said fixation device comprises an interface unit adapted to be fixated in relation to an adaptor unit for connection to the treatment unit, or which is adapted be fixated in relation to a frame for connection to the medical device. Said fixation device further comprises a sliding plate which is slidable in relation to said interface unit in an xz-plane of a coordinate system, wherein said system is a Cartesian coordinate system defined by three orthogonal axis having an x-axis extending in the medial-lateral direction of the patient, an y-axis extending in the anterior-posterior direction, and a z-axis extending in the cranial-caudal direction. Furthermore, said fixation device comprises a plate locking means for locking said sliding plate in relation to said interface unit, a bite-block for being inserted into a mouth of the patient, a linking means for linking said bite-block with said sliding plate, at least one pivot point arranged such that the bite-block is movable at least in a plane orthogonal to the xz-plane, and a link locking means for locking said at least one pivot point in a desired position in relation to said linking means so as to fixate the bite-block to the interface unit.

According to a second aspect of the present invention, there is provided a method for immobilizing a head of a patient relative a treatment unit during treatment of the head. Said method comprises the steps of: providing an interface unit adapted to be fixated in relation to an adaptor unit for connection to the treatment unit, or which is adapted to be fixated in relation to a frame for connection to the medical device; providing a sliding plate which is adapted to be slidable in relation to said interface unit in an xz-plane of a coordinate system. Said system is a Cartesian coordinate system defined by three orthogonal axis having an x-axis extending in the medial-lateral direction of the patient, an y-axis extending in the anterior-posterior direction, and a z-axis extending in the cranial-caudal direction. Furthermore, said method further comprises the steps of: providing a plate locking means adapted to lock said sliding plate in relation to said interface unit; providing a bite-block adapted to be inserted into a mouth of the patient; providing a linking means adapted to link said bite-block with said sliding plate; providing at least one pivot point arranged such that the bite-block is movable in a plane orthogonal to the xz-plane; providing a link locking means adapted to lock said at least one pivot point in a desired position in relation to said linking means so as to fixate the bite-block to the interface unit; positioning the bite-block in a co-operating position with a portion of the mouth using the slidable plate and the linking means; and fixating the positioning arrangement using the plate locking means and link locking means, thereby fixating the slidable plate and linking means, respectively.

Thus, the present invention is based on the idea of using a sliding plate slidable in a xz-plane of a coordinate system combined with a linking means pivotally movable in a plane orthogonal to the xz-plane for freely positioning of a bite-block in a co-operating position with the upper palate of a mouth, or at least a portion thereof, of a patient and thereafter fixating the bite-block in relation to the interface unit using easily accessible and lockable locking means thereby enabling a quick fixation of the fixation device in a desired position, which, in turn, provides for an accurate and repeatable immobilisation of a head of a patient during treatment thereof. In addition, a tensionless fixation is easily achieved as well as comfortable treatment position of the patient, which provides for a high repositioning accuracy. Moreover, the linking means entails that less material is situated in-front of the face of a patient during the treatment which ensures less artefacts in a radiation therapy result.

It should be noted that the term "immobilizing" as used herein is intended to refer to an element, i.e. the head of the patient, that is fixated by means of mechanical means, i.e. the fixation device, to reduce or eliminate motion thereof. In other words, the immobilized head is maintains its position relative to the therapy unit via interface unit or the like.

Moreover, it should also be noted that the term "treatment" as used herein, e.g. "treatment unit", "treatment system" or "treatment of the head", is intended to refer to any kind of diagnosis, therapy or surgery inside the head of the patient, e.g. MRI, Biopsy, neurological diagnosis, therapy or surgery, or various radiation therapy treatment or the like. Thus, a treatment unit may for example be a radiation therapy unit, proton therapy unit, ultrasound therapy or the like. The embodiments of the invention are suitable for a fractionated treatment, e.g. a fractionated radiation therapy.

Also, the term "medical device" as used herein is intended to refer to any kind of devices used for diagnosis, therapy or surgery inside the head of the patient, e.g. a biopsy needle or the like.

It should also be noted that the term "frame" as used herein is intended to refer to an element for supporting another element, e.g. for supporting a medical device. In such a case, the frame, for instance a stereotactic frame, provides a support for the medical device that is used for performing said treatment.

According to an embodiment of the present invention, said at least one pivot point comprises a first shaft arranged on said sliding plate, the first shaft being parallel with said xz-plane, a second shaft arranged on the bite-block, the second shaft being parallel with the first shaft and being arranged outside the mouth when the bite-block is positioned in the mouth. Thus, the sliding plate which is slidable in the xz-plane is provided with a first shaft that is parallel with the xz-plane and the bite-block is provided with a second shaft that is parallel with the first shaft. Thereby, the first and second shafts are in an pivotal engagement with the parallel arranged link elements of the linking means such that the bite-block is movable in plane orthogonal to the xz-plane.

As is understood, in an embodiment of said fixation device wherein said at least one pivot point comprises a first and second shaft may also be provided by additional pivot points in between the first and second shaft such that the bite-block is movable at least in a plane orthogonal to the xz-plane.

In another embodiment of the present invention, said fixation device comprises at least a first pivot point between said sliding plate and said linking means and at least a second pivot point between said bite-block and said linking means for pivotally engaging the linking means with the sliding plate and bite-block, respectively, such that the bite-block is movable at least in a plane orthogonal to the xz-plane. Alternatively, and as mentioned above, in the embodiment wherein said fixation device comprises a first and second pivot point, additional pivot points may be provided such that movability of the fixation device is enhanced. Additionally, said pivot point is selected from a group comprising a socket-and-ball joint or hinge joint. Thus, in an example embodiment of the fixation device, the first pivot point may be a hinge joint, such as a shaft or the like, and the second pivot point may be a socket-and-ball-joint. As is understood, the joints may be contrarily arranged.

In an embodiment of the present invention, the linking means comprises two parallel elongated link elements which are pressed together for pivotally holding the first and second shafts in a first and second recesses at opposite elongated ends for co-operation with said first and second shaft, whereby the bite-block is movable in a plane orthogonal to the xz-plane.

Said elongated elements, such as bars or the like, are arranged to provide a elongate extension, besides linking or connecting the first and second shafts together. Thus the first and second shaft are connected at the two most distally arranged ends the elongated linking means or elements. Furthermore, as mentioned above, the shafts and the elements are fixated to each other by means of frictional forces, i.e. the contact surfaces of the connection thereof provides a high friction against each other.

In a further embodiment of the present invention, the link locking means comprises screw means such that a force presses the elongated link elements together such that the first and second shafts are locked in position in relation to the link elements, and wherein the screw means is arranged such that said screw means can be operated from the side opposite the side facing the patient during a fixation operation prior to the treatment. The screw means, i.e. the means for locking the shafts and linking means in position relative to each other, are arranged to achieve an easy locking thereof.

According to an embodiment of the present invention, a contact surface of the link elements and the first and second shaft which are in contact is a frictional surface for frictional locking of the first and second shaft in position relative the link elements. This achieves a continuously variable locking of the first and second shafts which contributes to a tensionless fixation.

In an embodiment of the present invention, the linking means is adjustable in a direction parallel to an axis extending through the first and second shaft for adjusting the distance between the first and second shaft. Thus, the linking means may is adjusted in a telescopic manner, i.e. in a elongation and compression manner, to adjust the length of the linking means portion between the first and second shafts, i.e. to adjust the linking distance or length between the shafts. This contributes to a tensionless fixation even further.

In one embodiment of the present invention, the interface unit is adapted to be removably connected to an adaptor unit or a frame. Alternatively, or in combination with a removable interface unit, in an embodiment, the adaptor unit is adapted to be removably connected to said treatment unit. The immobilization or fixation, which are individual for each patient, can be preserved by means of the removable interface unit thereby ensuring that the patient can be docked to the radiation therapy unit in a repeatable way to guarantee that the patient is positioned in exact alignment to a reference position at every single treatment session. Also, the removable adaptor unit that is removably connected to the treatment unit further ensures that the patient can be, in a repeatable manner, docked to the radiation therapy unit or the like.

In one embodiment of the present invention, the interface unit is removably connected to the adaptor unit by means of fastening means, wherein the fastening means is arranged such that said fastening means can be operated from a side opposite a side facing the patient during a fixation operation prior to the treatment. An easy locking of the removable interface unit is thereby ensured. Thus, the interface unit is removably fastened or connected to the adaptor unit such that an easy connection, removal and re-connection of the interface unit to the adaptor unit is achieved. Furthermore, the fastening means are easily operated such that the fastening means may fastened while the patient is being supervised.

In one embodiment of the present invention, the plate locking means comprises pressure means for pressing the sliding plate against the interface unit for frictionally locking the sliding plate. This achieves a continuously variable adjustment of the sliding plate which contributes to a tensionless fixation. Thus, the means for locking the slidable plate comprises means for pressing or forcing the slidable plate into a fictional connection with the interface unit, i.e. the slidable plate is locked in position by means of friction forces.

According to an embodiment of the present invention, the pressure means comprises a locking plate facing the sliding plate and a screw means such that a force is exerted against the locking plate which presses the sliding plate against the interface unit, and wherein the screw means is arranged such that said screw means can be operated from the side opposite the side facing the patient during a fixation operation prior to the treatment. This contributes to an easy locking of the removable frame. The pressure plate which is forced or pressed against the slidable plate ensures an evenly distributed exerting force from the slidable plate to the interface unit, thereby an accurate and reliable locking of the slidable plate relative the interface unit is achieved.

In an embodiment of the method of present invention, the step of providing at least one pivot point comprises the steps of providing a first shaft arranged on said sliding plate, the first shaft being parallel with said xz-plane, providing a second shaft arranged on the bite-block, the second shaft being parallel with the first shaft and being arranged outside the mouth when the bite-block is positioned in the mouth.

Thus, the provision of the first shaft that is parallel with the xz-plane and the second shaft that is parallel with the first shaft, provides a bite-block that is movable at least in a plane orthogonal to the xz-plane. Furthermore, said method may comprise the steps of providing additional pivot points in between the first and second shaft.

In an embodiment of the method of present invention, the step of providing a linking means adapted to link said bite-block comprises the step of providing linking means having two parallel elongated link elements which are pressed together for pivotally holding the first and second shafts in a first and second recesses at opposite elongated ends for co-operation with said first and second shaft, whereby the bite-block is movable in a plane orthogonal to the xz-plane.

According to an embodiment of the method of the present invention, the method further comprises a step of releasing the patient from the bite-block and the interface unit from the adaptor unit or frame. Thus, after completion of at least a first precise and accurate treatment session the patient is released from the bite-block and the fixation device. Alternatively, thereafter the step of releasing the patient from the bite-block and interface unit from the adaptor unit or frame further comprises the steps of: re-fixating the patient relatively the interface unit by means of inserting the bite-block and thereafter re-fixating the interface unit relative to the adaptor unit or frame. The adjustment of the head fixation, which is individual for each patient, can thereby be preserved. Thus, the patient can be docked to the treatment unit, e.g. radiation therapy unit in a repeatable way to guarantee that the patient is positioned and repositioned in exact alignment to a reference position at every single treatment session.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

Preferred embodiments of the invention will now be described in greater detail with reference to the accompanying drawings, in which.

DESCRIPTION OF PREFERRED EMBODIMENTS

First, with reference to FIGS. 1-3, a radiation therapy system for which the present invention is applicable comprises a radiation therapy unit or radiation unit 10 and a patient positioning unit 20 will be described. In the radiation unit 10, there are provided radioactive sources, radioactive source holders, a collimator body, and external shielding elements. The collimator body comprises a large number of collimator channels directed towards a common focus point, in a manner as is commonly known in the art.

The collimator body also acts as a radiation shield preventing radiation from reaching the patient other than through the collimator channels. Examples of collimator arrangements in radiation therapy systems applicable to the present invention can be found in U.S. Pat. No. 6,931,096, which is hereby incorporated herein by reference in its entirety. However, the present invention is also applicable to radiation therapy systems using other arrangements for collimating radiation into a fixed focus point, such as is disclosed in U.S. Pat. No. 4,780,898. Furthermore, the present inventions is also applicable to LINAC radiosurgical systems, in which a collimated x-ray beam is focused on a stereotactically identified intracranial target and the gantry of the LINAC rotates around the patient, producing an arc of radiation focused on the target.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit, or interface unit, either directly or via an adaptor unit 42, see FIG. 3. A head can according to the present invention, for example, a rigid casing enclosing the head of the patient (which will be described in more detail below with reference to FIGS. 4 and 5) is attachable to the patient fixation frame, see FIG. 3.

The coordinates of the fixation unit is defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system.

The fixation arrangement 28 comprises two engagement points 30, 32, which are arranged for preventing the patient fixation unit from translational and/or rotational movement in relation to the movable carriage 24.

Figure 1:
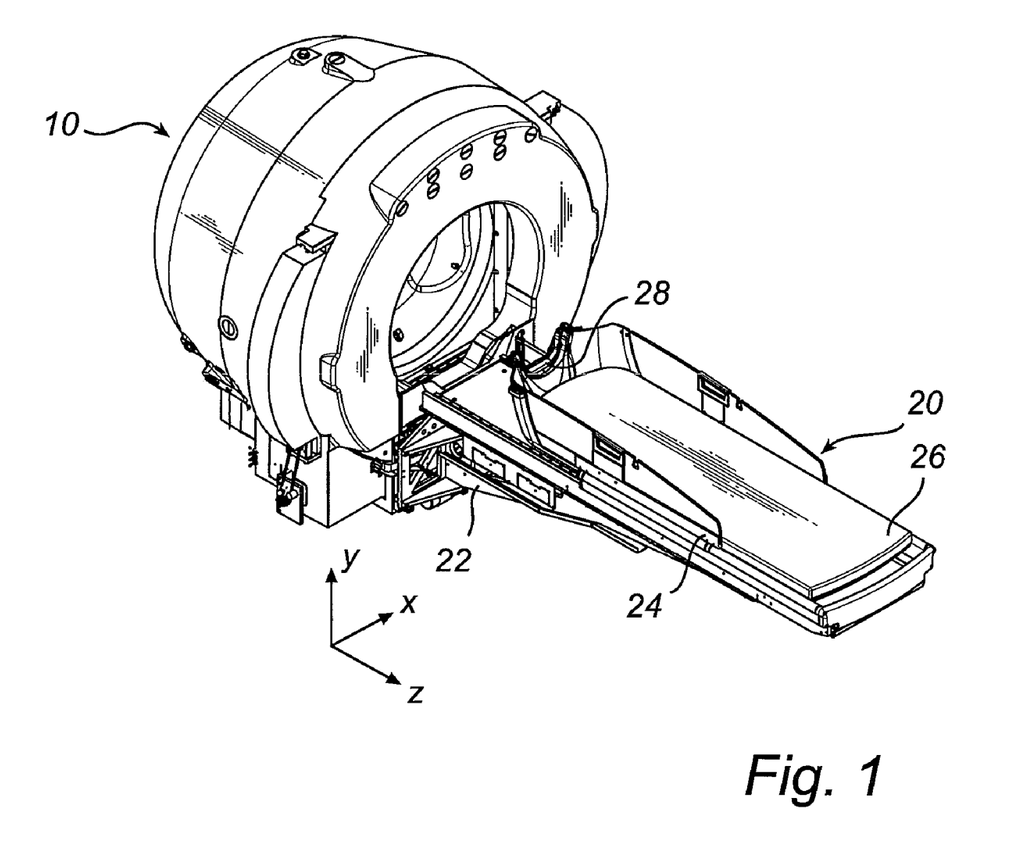
FIG. 1 illustrates the general principle of a radiation therapy system in which the present invention may be used.
Figure 2:
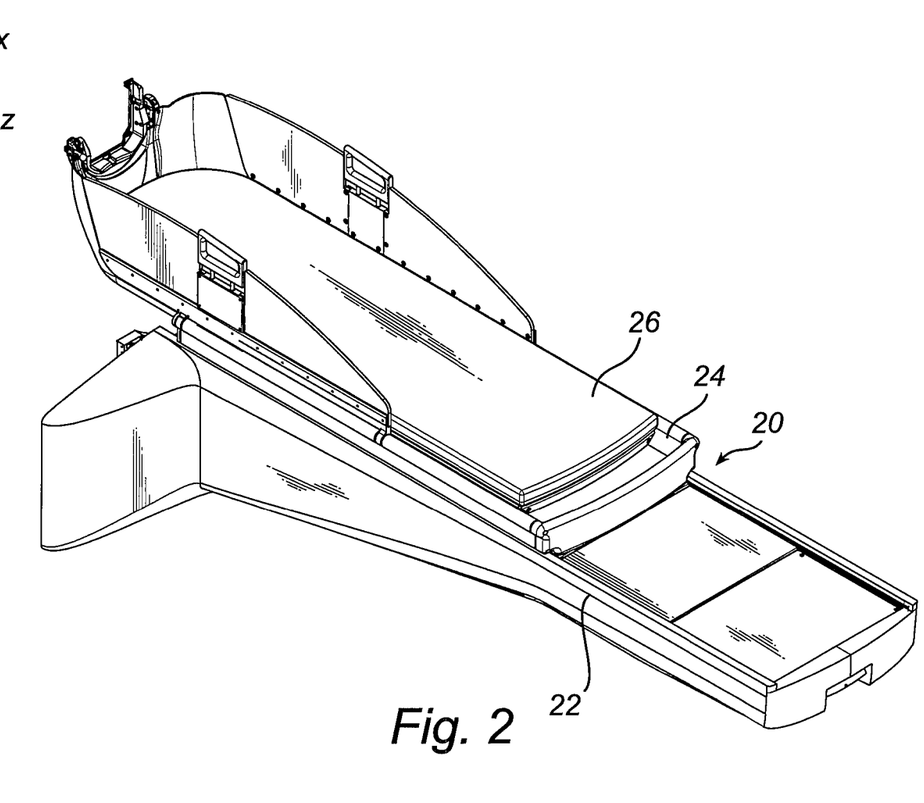
FIG. 2 illustrates the positioning unit used in the system of FIG. 1.
Figure 3:
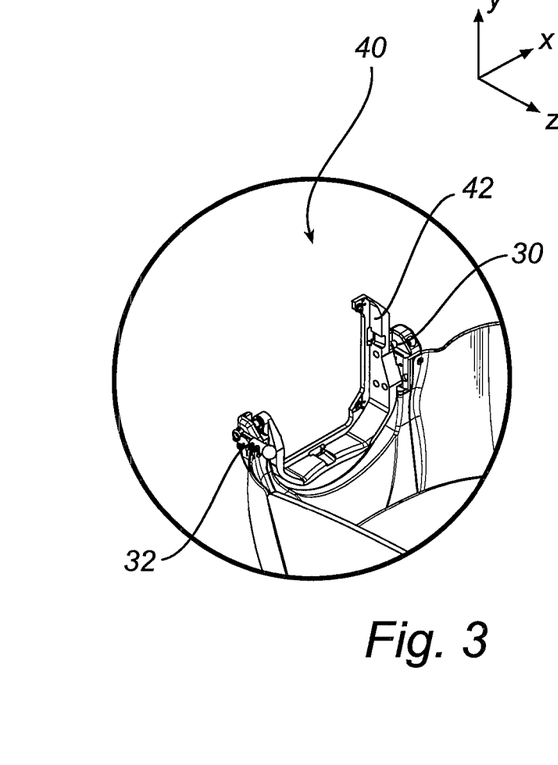
FIG. 3 illustrates a part of the positioning unit including the engagement points for holding a fixation frame in more detail.

As can be understood from FIGS. 1 and 2, the described embodiment concerns a radiation therapy system for providing gamma radiation therapy to a target volume in the head of human patient. Such therapy is often referred to as stereotactic radiation surgery. During therapy, the patient head is fixed in a fixation unit in the form of a stereotactic head frame, which comprises engagement points adapted for engagement with the engagement points 30, 32 of the radiation therapy system. Thus, during the stereotactic radiation surgery, the head of the patient is fixed in the stereotactic frame, which in turn is fixedly attached to the patient positioning unit via the engagement points 30, 32. During movement of the treatment volume in the head of the patient in relation to the radiation focus point, along the three orthogonal axes x, y, and z shown in FIG. 1, the entire patient is moved along the axes. Thus, there is no relative movement between the head frame and the carriage 24 of the patient positioning unit 20.

Figure 4:
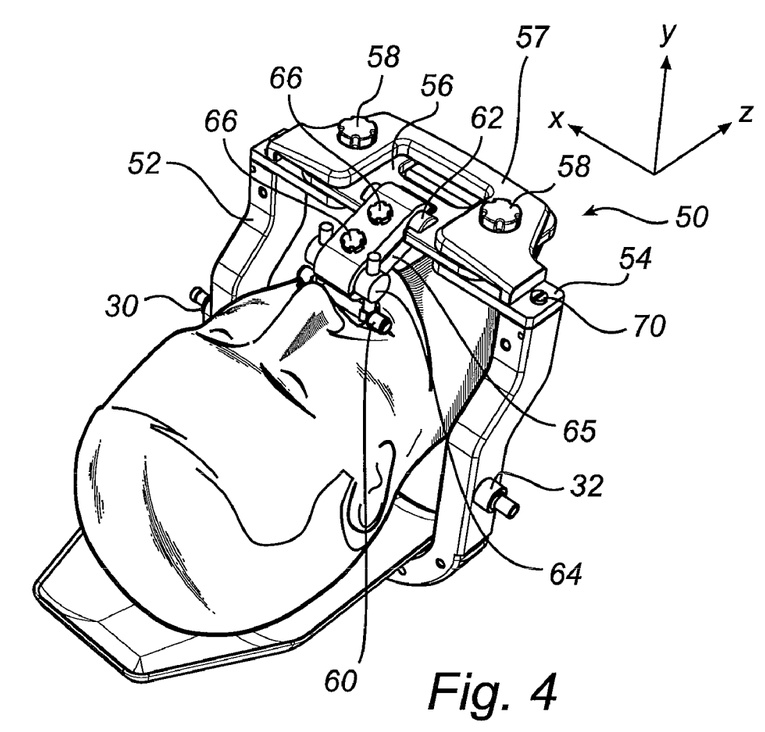
FIG. 4 illustrates a fixation device according to an embodiment of the present invention and part of the positioning unit.
Figure 5:
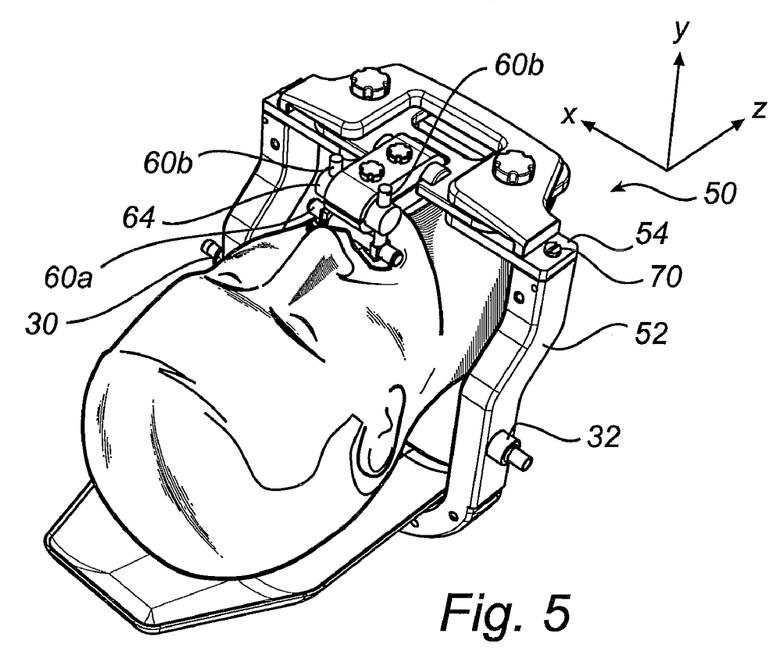
FIG. 5 illustrates the fixation device and part of the positioning unit of FIG. 4, wherein the fixation device is immobilizing a larger head than the head of FIG. 4.

With reference to FIGS. 4 and 5, a fixation device 50 is shown. The head being fixated in FIG. 5 is larger than the head of the patient in FIG. 4, which results in a different fixation configuration of the fixation device 50, or in different fixation parameters of the radiation therapy unit, i.e. radiation therapy system. The fixation device 50 of FIGS. 4 and 5 is connected to an adaptor unit 52, which via engagement points 30 and 32 is connected to the patient positioning unit 20 of the radiation therapy system. Thus, the adaptor unit is a part of the patient positioning unit 20. As is understood, the fixation device 50 may also, without any adaptor unit, be directly connected to the positioning unit 20. Consequently, the head of the patient is immobilized to the carriage 24 of the patient positioning unit 20 by means of the fixation device.

In FIG. 4 there is shown a fixation device 50 for immobilizing a head of a patient relative a radiation therapy unit during neurological diagnosis, therapy or surgery. The fixation device 50 comprises an interface 54 adapted to be fixated in relation to the radiation therapy unit via engagement points 30 and 32, adaptor unit or frame 52 and the slidable or movable carriage 24. Interface unit 54 is removably connected to the adaptor unit 52. A sliding plate 56 is connected to the interface unit 54 in a slidable or movable manner, such that the sliding plate 56 is slidable or movable in relation to the interface unit 54 in an xz-plane of a Cartesian coordinate system.

Part from being an adaptor arrangement between the interface unit 54 and the fixation arrangement of a radiation treatment system, it is to be understood that the adaptor unit or frame 52 herein described and shown may also be a frame for supporting medical devices, such as a biopsy needle device or the like.

Such a Cartesian coordinate system is defined by three orthogonal axis having an x-axis extending in the medial-lateral direction of the patient, an y-axis extending in the anterior-posterior direction, and a z-axis extending in the cranial-caudal direction.

Furthermore, in FIG. 4 a first shaft 62 is shown, which is parallel with said xz-plane. The first shaft 62 is connected to the sliding plate 56. A plate locking means lock the sliding plate 56 in relation to the interface unit 54 of the fixation device 50. The plate locking means in FIGS. 4-6 comprises a plate-like means 57 adapted to transmit a pressure force exerting from a pair of screws 58 to the sliding plate 56. Thus, the screws 58 locks the sliding plate 56 in between the interface unit 54 and the plate-like means 57. Preferably, the surfaces in contact are coated with or made of a frictional material, such that the intermediate plate 56 is frictionally locked in position. A bite-block 60 can be inserted into a mouth of the patient and is adapted to co-operate with the upper palate of the mouth (not shown). The bite-block is provided with a second shaft 64, which is parallel with the first shaft 62. Moreover, the first and second shaft 62 and 64 are pivotally interconnected by means of a linking means 65. Such a pivotal engagement where the first shaft 62 is linked to the second shaft 64 enables a double-pivotal movement of the bite-block 60. In operation, i.e. when the bite-block is inserted into the mouth of the patient and co-operates with the upper palate, the bite-block 60 is pivotally movable in a plane orthogonal to the axes of the first and second shafts. Furthermore, the linking means 65 is provided with a link locking means 66 for locking the first and second shafts 62 and 64 in relation to said linking means 65, thereby fixating the bite-block in position in relation to the interface unit 54 of the fixation device 50.

In this illustrated embodiment, the link locking means 66 in FIGS. 4 and 5 are a pair of screws. However, as is understood by a skilled person, other suitable locking means may be used such that the first and second shafts are locked in position relative the linking means 65.

In use, only a portion of the bite-block 60 is visible, as shown in FIGS. 4 and 5. This is best seen in FIG. 5, where an external bite-block portion 60a of the bite-block 60 outside the mouth connects the second shaft 64 by means of two protruding portions 60b. The protruding portions 60b are in orthogonal engagement with the second shaft, preferably on either side of the linking means 65. Although the inserted portion, or internal portion, of the bite-block is not seen in FIGS. 4 and 5, an example embodiment of a bite-block comprises an upper surface, or at least a portion, which co-operates with the upper palate of the mouth. The internal portion is connected to an external portion for connection with the fixation device. Thus, the bite-block of the invention may have any suitable shape as long as it fits the shape of the mouth cavity, such as a shape corresponding to the shape of the upper part of the mouth cavity of the patient.

As mentioned above, the bite-block is adapted to co-operate with the upper palate of the mouth when inserted. However, the bite-block may co-operate with another portion of the mouth, other than the upper palate. Preferably, such a portion is connected to the skull or cranium, such that a fixation of the bite-block results in a fixation of the skull or cranium, or more specifically, the intracranial target.

The linking means 65 in FIGS. 4 and 5 comprises a pair of parallel arranged elongated link elements which are in pivotal engagement with the first and second shafts 62 and 54 at either end of the link elements. Alternatively, the linking means may also be adjustable in a linking direction for adjusting the distance between the first and second shaft, i.e. in a direction that extends along the elongated element. Thus, the shafts may be moved in a telescopic manner in relation to each other. Furthermore, the linking means may also be comprised of a single elongated element which, at its distal ends, pivotally engages the first and second shafts. Also, the single elongated element may also be telescopic. In operation, when the bite-block is in position, i.e. in co-operation with the upper palate of the mouth, the position of the bite-block is fixated by tighten the link locking means 66, in the illustrated embodiment screws are used, forcing the link elements together, thereby frictionally locking the positions of the shafts 62 and 64 in relation to the linking means 65 or link elements.

In the embodiment shown in FIGS. 4 and 5, the removably connected interface unit 54 of the fixation device 50 is fixated to the carriage 24 of the patient positioning unit 20 by means of an interface unit locking means 70, which in the embodiment of FIGS. 4 and 5 comprises a pair of screws at opposite ends of the interface unit 54 (only one screw is shown).

Referring to FIG. 5, the fixation device of FIG. 4 is shown, which immobilizes a larger head than the device of FIG. 4. The removable interface unit 54 is connected to the adaptor unit 52 at a position different from the position in FIG. 4, and locked to the adaptor unit 52 by means of the locking means 70. Although two locking positions for locking the interface unit 54 to the adaptor 52 is shown in FIGS. 4 and 5, more locking positions may be provide, as well as other locking arrangement.

Figure 6:
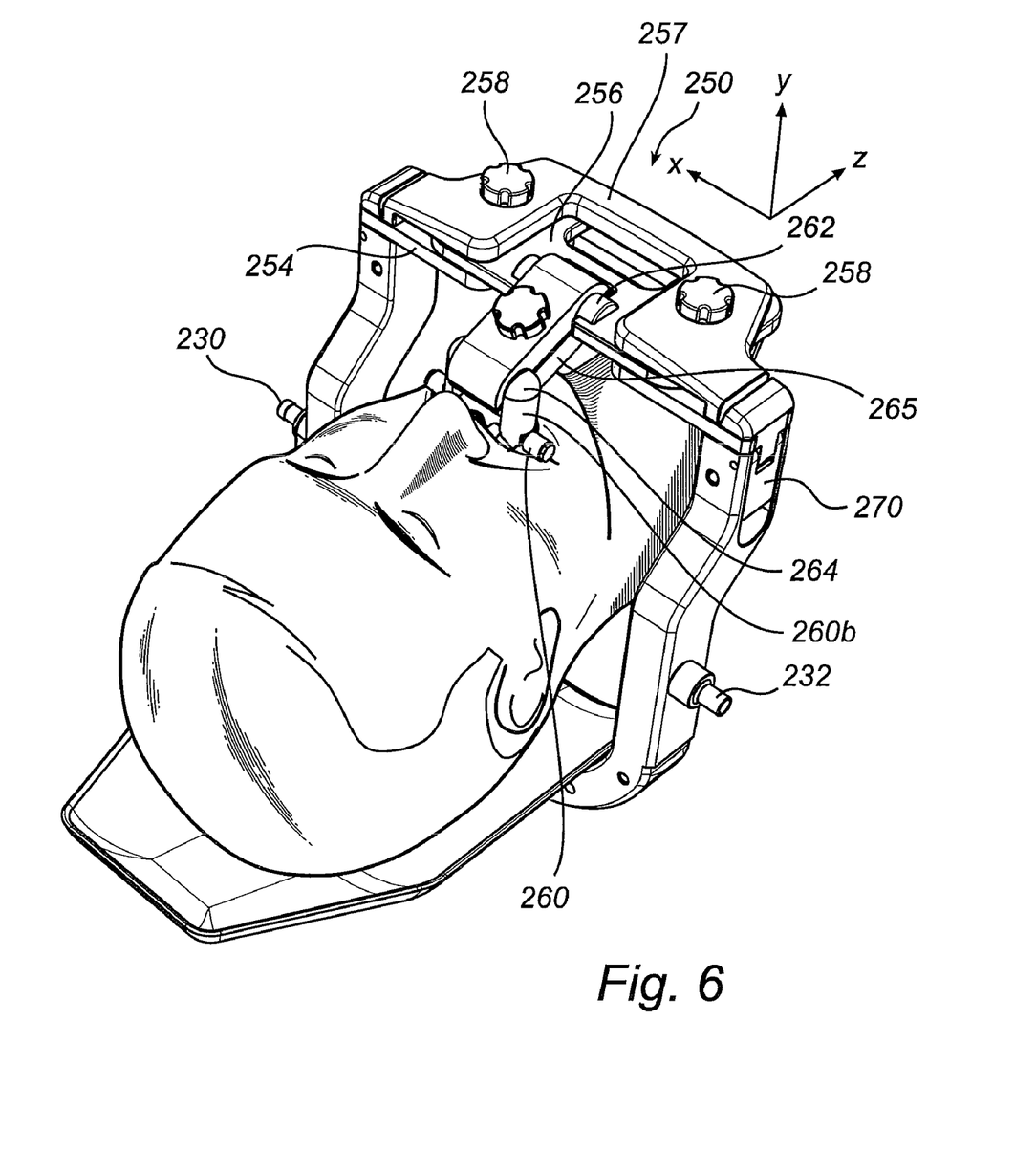
FIG. 6 illustrates the fixation device according to another embodiment of the present invention.

In FIG. 6 there is shown another example embodiment of a fixation device 250 for immobilizing a head of a patient relative a radiation therapy unit during neurological diagnosis, therapy or surgery. The fixation device 250 comprises an interface unit 254 adapted to be fixated in relation to the radiation therapy unit via engagement points 230 and 232, adaptor unit 252 and the slidable or movable carriage 24 (not shown). Interface unit 254 is removably connected to the adaptor unit 252 by means of an interface unit locking means 270. In FIG. 6, the interface unit locking means comprises a pair of ratchet and pawl means. However, the interface unit locking means may also be a snap locking means. A sliding plate 256 is connected to the interface unit 254 in a slidable or movable manner, such that the sliding plate 256 is slidable or movable in relation to the interface unit 254 in an xz-plane of a Cartesian coordinate system.

As the fixation device 50 in FIG. 4, the fixation device 250 comprises a first shaft 262 is shown, which is parallel with said xz-plane. The first shaft 262 is connected to the sliding plate 256. As in FIGS. 4-5, the plate locking means comprises a plate-like means 257 adapted to transmit a pressure force exerting from a pair of screws 258 to the sliding plate 256, locking the sliding plate 256 in between the interface unit 254 and the plate-like means 257. A bite-block 260 can be inserted into a mouth of the patient and is adapted to co-operate with the upper palate of the mouth (not shown). The bite-block is provided with a second shaft 264, which is parallel with the first shaft 262. In FIG. 6, the second shaft is integrated with the protruding portions 260b of the bite-block 260 (cf. FIGS. 4 and 5). Moreover, the first and second shaft 262 and 264 are pivotally interconnected by means of a linking means 265. Here, the link locking means 266 for locking the first and second shafts 262 and 264 in relation to said linking means 265, comprise only one screw means, in comparison to locking means 66 of fixation device 50. Consequently, in the fixation device 250 the bite-block is fixated in position in relation to the interface unit 254 by means of only three screwing means.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

The invention claimed is:

1. A fixation device for immobilizing a head of a patient relative a treatment unit or medical device during treatment of the head, said fixation device comprising an interface unit adapted to be fixated in relation to an adaptor unit for connection to the treatment unit, or to a frame for connection to the medical device;

a sliding plate configured to be slidable in relation to said interface unit in an xz-plane of a coordinate system, said system being a Cartesian coordinate system defined by three orthogonal axis having an x-axis extending in the medial-lateral direction of the patient, an y-axis extending in the anterior-posterior direction, and a z-axis extending in the cranial-caudal direction;

a plate locking device configured to lock said sliding plate in relation to said interface unit;

a bite-block configured to be inserted into a mouth of the patient;

a linking device configured to link said bite-block with said sliding plate;

at least one pivot point arranged such that the bite-block is movable at least in a plane orthogonal to the xz-plane; and a link locking device configured to lock said at least one pivot point in a desired position in relation to said linking device so as to fixate the bite-block to the interface unit.

2. The fixation device according to claim 1, wherein said at least one pivot point comprises a first shaft arranged on said sliding plate, the first shaft being parallel with said xz-plane, a second shaft arranged on the bite-block, the second shaft being parallel with the first shaft and being arranged outside the mouth when the bite-block is positioned in the mouth.

3. The fixation device according to claim 2, wherein said pivot point is selected from a group comprising a socket-and-ball joint or hinge joint.

4. The fixation device according to claim 1, wherein said fixation device comprises at least a first pivot point between said sliding plate and said linking device and at least a second pivot point between said bite-block and said linking device for pivotally engaging the linking device with the sliding plate and bite-block, respectively, such that the bite-block is movable at least in a plane orthogonal to the xz-plane.

5. The fixation device according to claim 4, wherein said pivot point is selected from a group comprising a socket-and-ball joint or hinge joint.

6. The fixation device according to claim 1, wherein said pivot point is selected from a group comprising a socket-and-ball joint or hinge joint.

7. The fixation device according to claim 1, wherein the linking device comprises two parallel elongated link elements which are pressed together for pivotally holding a first and second shafts in a first and second recesses at opposite elongated ends for co-operation with said first and second shaft, whereby the bite-block is movable in a plane orthogonal to the xz-plane.

8. The fixation device according to claim 7, wherein the link locking device comprises a screw such that a force presses the elongated link elements together such that the first and second shafts are locked in position in relation to the two parallel elongated link elements, and wherein the screw is configured to be operated from the side opposite the side facing the patient during a fixation operation prior to the treatment.

9. The fixation device according to claim 7, wherein a contact surface of the two parallel elongated link elements and the first and second shafts which are in contact is a frictional surface for frictional locking of the first and second shafts in position relative the two parallel elongated link elements.

10. The fixation device according to claim 1, wherein the linking device is adjustable in a direction parallel to an axis extending through a first and second shafts for adjusting the distance between the first and second shafts.

11. The fixation device according to claim 1, wherein the interface unit is adapted to be removably connected to an adaptor unit or a frame.

12. The fixation device according to claim 1, wherein the adaptor unit is adapted to be removably connected to said treatment unit.

13. The fixation device according to claim 1, wherein the interface unit is removably connected to the adaptor unit by a fastening device wherein the fastening device is configured to be operated from a side opposite a side facing the patient during a fixation operation prior to the treatment.

14. The fixation device according to claim 1, wherein the plate locking device comprises a pressing device configured to press the sliding plate against the interface unit for frictionally locking the sliding plate.

15. The fixation device of claim 14, wherein the pressing device comprises a locking plate facing the sliding plate and a screw such that a force is exerted against the locking plate which presses the sliding plate against the interface unit, and wherein the screw is configured to be operated from the side opposite the side facing the patient during a fixation operation prior to the treatment.

16. A method for immobilizing a head of a patient relative a treatment unit during treatment of the head, said method comprising the steps of:

providing an interface unit adapted to be fixated in relation to an adaptor unit for connection to the treatment unit, or to a frame for connection to the medical device;

providing a sliding plate adapted to be slidable in relation to said interface unit in an xz-plane of a coordinate system, said system being a Cartesian coordinate system defined by three orthogonal axis having an x-axis extending in the medial-lateral direction of the patient, an y-axis extending in the anterior-posterior direction, and a z-axis extending in the cranial-caudal direction;

providing a plate locking device adapted to lock said sliding plate in relation to said interface unit;

providing a bite-block adapted to be inserted into a mouth of the patient;

providing a linking device adapted to link said bite-block with said sliding plate;

providing at least one pivot point arranged such that the bite-block is movable in a plane orthogonal to the xz-plane;

providing a link locking device adapted to lock said at least one pivot point in a desired position in relation to said linking means so as to fixate the bite-block to the interface unit;

positioning the bite-block in a co-operating position with a portion of the mouth using the slidable plate and the linking device; and fixating the positioning arrangement using the plate locking device and link locking device, thereby fixating the slidable plate and linking device, respectively.

17. The method according to claim 16, wherein the step of providing at least one pivot point comprises the steps of providing a first shaft arranged on said sliding plate, the first shaft being parallel with said xz-plane; and providing a second shaft arranged on the bite-block, the second shaft being parallel with the first shaft and being arranged outside the mouth when the bite-block is positioned in the mouth.

18. The method according to claim 16, wherein the linking device comprises two parallel elongated link elements which are pressed together for pivotally holding a first and second shafts in a first and second recesses at opposite elongated ends for co-operation with said first and second shaft, whereby the bite-block is movable in a plane orthogonal to the xz-plane.

19. The method according to claim 16, further comprising the step of releasing the patient from the bite-block and the interface unit from the adaptor unit or frame.

20. The method according to claim 19, wherein the step of releasing the patient from the bite-block and interface unit from the adaptor unit or frame further comprises the steps of: re-fixating the patient relative to the interface unit by means of inserting the bite-block and thereafter re-fixating the interface unit relative to the adaptor unit or frame.

\* \* \* \* \*